US012646611B1

(12) United States Patent
Alhijji et al.

(10) Patent No.: US 12,646,611 B1
(45) Date of Patent: Jun. 2, 2026

(54) ROTARY INSTRUMENT STORAGE, MONITORING, AND ACCESS CONTROL SYSTEM

(71) Applicant: KING SAUD UNIVERSITY, Riyadh (SA)

(72) Inventors: Saleh Mohammed Alhijji, Riyadh (SA); Faisal Fawaz Alanazi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/392,776

(22) Filed: Nov. 18, 2025

(51) Int. Cl.
| | |
|---|---|
| *G16H 40/40* | (2018.01) |
| *A61C 1/00* | (2006.01) |
| *A61C 3/06* | (2006.01) |
| *A61C 19/02* | (2006.01) |
| *G06F 21/31* | (2013.01) |

(52) U.S. Cl.
CPC ........... *G16H 40/40* (2018.01); *A61C 1/0015* (2013.01); *A61C 3/06* (2013.01); *A61C 19/02* (2013.01); *G06F 21/31* (2013.01)

(58) Field of Classification Search
CPC .............................. B65D 25/10; B65D 25/108
See application file for complete search history.

(56) References Cited

U.S. PATENT DOCUMENTS

| | | | |
|---|---|---|---|
| 5,006,066 | A | 4/1991 | Rouse |
| 5,435,979 | A | 7/1995 | Miller et al. |
| 6,328,565 | B1 | 12/2001 | Rose |
| 6,681,925 | B2 | 1/2004 | Fischer et al. |
| 6,719,560 | B2 | 4/2004 | Capt |
| 8,074,799 | B2 | 12/2011 | Fujii et al. |
| 10,987,205 | B2 * | 4/2021 | DeBord ................. A61B 50/31 |
| 11,850,116 | B2 * | 12/2023 | Schlueter ............... A61C 8/009 |
| 12,179,334 | B2 | 12/2024 | Chuang |

* cited by examiner

*Primary Examiner* — Bryon P Gehman
(74) *Attorney, Agent, or Firm* — Nath, Goldberg & Meyer; Joshua B. Goldberg

(57) ABSTRACT

A smart storage and access control system for rotary instruments such as dental burs is provided. The system includes a base with at least one collet configured to secure or release a rotary instrument. A user authenticator is included to verify user identity and authorization, as well as a controller operatively connected to the authenticator and collet. Upon verification, the controller signals the collet to release or retain a rotary instrument associated with a user. The system may include sensors for detecting instrument presence, visual indicators for status display, and a protective cover that disables release when open. A cam-driven collet mechanism converts motor rotation into linear movement for secure clamping. The controller may record access data in a tamper-resistant digital ledger and analyze usage patterns using artificial intelligence to predict maintenance needs. The disclosed system and methods improve accountability, security, and reliability for usage of precision rotary instruments.

20 Claims, 5 Drawing Sheets

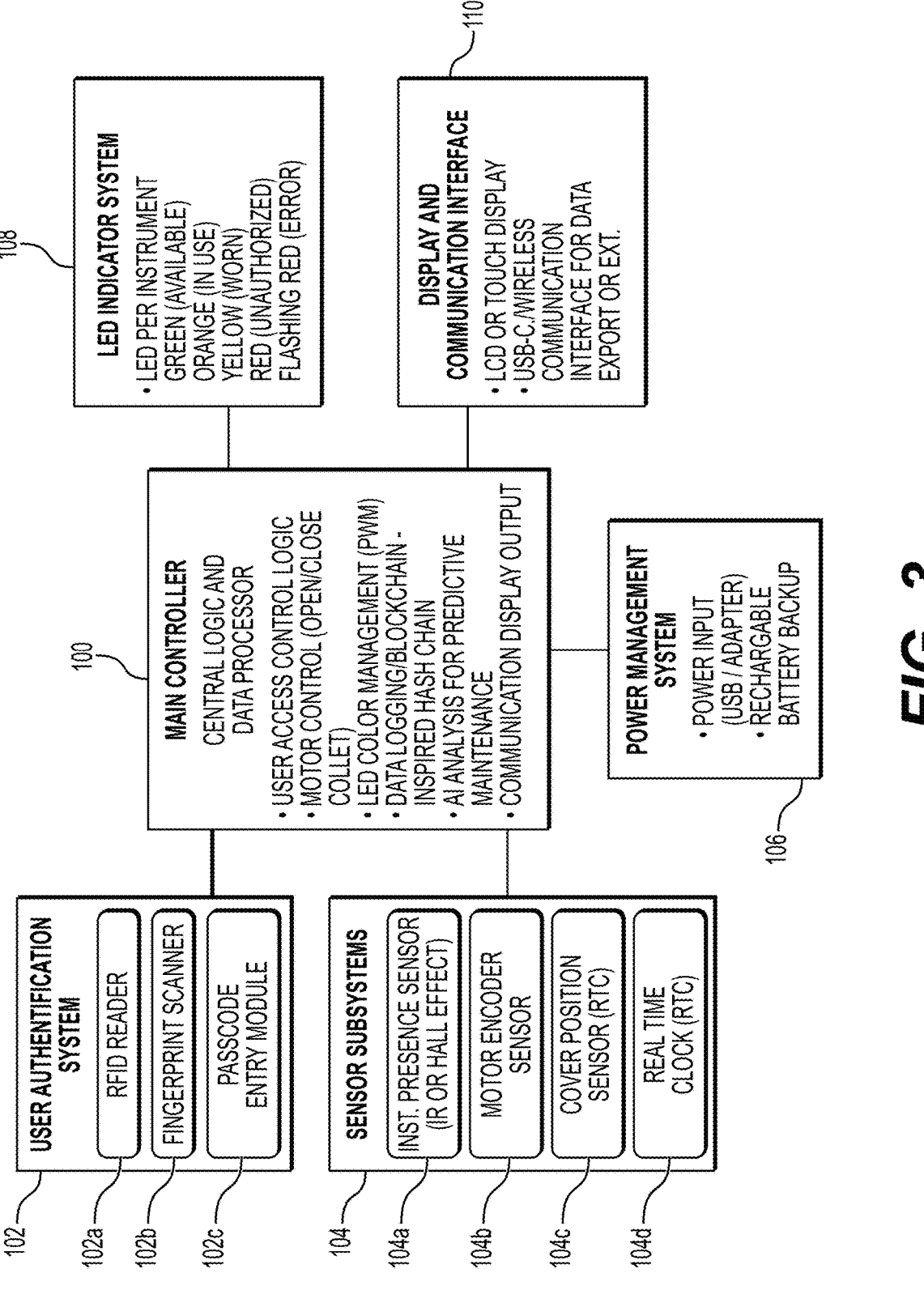

108

LED INDICATOR SYSTEM
- LED PER INSTRUMENT
  GREEN (AVAILABLE)
  ORANGE (IN USE)
  YELLOW (WORN)
  RED (UNAUTHORIZED)
  FLASHING RED (ERROR)

110

DISPLAY AND COMMUNICATION INTERFACE
- LCD OR TOUCH DISPLAY
- USB-C/WIRELESS COMMUNICATION
  INTERFACE FOR DATA EXPORT OR EXT.

100

MAIN CONTROLLER

CENTRAL LOGIC AND DATA PROCESSOR
- USER ACCESS CONTROL LOGIC
- MOTOR CONTROL (OPEN/CLOSE COLLET)
- LED COLOR MANAGEMENT (PWM)
- DATA LOGGING/BLOCKCHAIN - INSPIRED HASH CHAIN
- AI ANALYSIS FOR PREDICTIVE MAINTENANCE
- COMMUNICATION DISPLAY OUTPUT

106

POWER MANAGEMENT SYSTEM
- POWER INPUT (USB / ADAPTER)
- RECHARGABLE BATTERY BACKUP

102

USER AUTHENTIFICATION SYSTEM
- 102a RFID READER
- 102b FINGERPRINT SCANNER
- 102c PASSCODE ENTRY MODULE

104

SENSOR SUBSYSTEMS
- 104a INST. PRESENCE SENSOR (IR OR HALL EFFECT)
- 104b MOTOR ENCODER SENSOR
- 104c COVER POSITION SENSOR (RTC)
- 104d REAL TIME CLOCK (RTC)

FIG. 3

ROTARY INSTRUMENT STORAGE, MONITORING, AND ACCESS CONTROL SYSTEM

BACKGROUND

Field

The present disclosure relates to systems and methods for the secure storage, management, and access control of precision rotary instruments such as dental burs or other similar rotary tools.

Description of Related Art

Rotary instruments, such as dental burs, surgical drills, and similar precision tools, are essential components in clinical, laboratory, and educational environments. These instruments are typically small, delicate, and costly, requiring careful handling and frequent replacement. In busy workspaces, instruments are often misplaced, damaged, or lost due to inadequate storage and tracking systems. Conventional holders or storage trays offer only passive organization, providing no mechanism for access control, user authentication, or usage monitoring. As a result, institutions face significant challenges in maintaining inventory accuracy, enforcing accountability, and ensuring proper maintenance and hygiene standards.

Existing digital inventory systems are limited in their ability to physically secure instruments or verify individual user access. Likewise, automated dispensers and cabinets designed for general tools lack the precision handling and fine-scale control necessary for small rotary instruments. The absence of an integrated solution that combines mechanical security, digital authentication, and intelligent data analysis leads to inefficiencies, unnecessary costs, and compromised operational control.

Thus, systems and methods for storage, monitoring, and access control of rotary instruments solving the aforementioned problems are desired.

SUMMARY

The present disclosure provides a smart storage and access control system for rotary instruments, such as dental burs, drill bits, or other precision rotary tools. In one embodiment, the system includes a base including at least one collet configured to selectively secure or release a rotary instrument. Each rotary instrument includes a working end and a holding end adapted for insertion into the collet. A user authenticator, such as a fingerprint reader, radio-frequency identification (RFID) reader, facial recognition sensor, or passcode entry device, is configured to verify the identity and authorization level of a user. A controller, operatively connected to the user authenticator and the collet, manages access by signaling the collet to release or retain the rotary instrument upon successful user verification.

The controller may further enforce access rules, such as allowing retrieval of only a single instrument at a time until the previously removed instrument is returned. One or more sensors may detect the presence or absence of an instrument within its respective collet, while visual indicators, such as multicolor light-emitting diodes (LEDs), may provide status feedback to the user, including instrument availability, use status, error conditions, or maintenance alerts. A transparent protective cover may prevent access when closed, with associated sensors configured to detect its open or closed state and disable release of the rotary instrument when open, allowing for portability of the system without the instruments falling out of their respective collets.

In certain embodiments, the collet is actuated by a cam-driven mechanism that converts rotational motion from a motor into linear movement to clamp or release the rotary instrument. The mechanism may include a spur gear with a cam profile driven by a pinion gear coupled to a motor shaft, providing a mechanical advantage in actuating the cam. The collet itself may be spring biased and include slotted sections that radially compress around the rotary instrument's holding end when driven into a closed position. An anti-rotational guide may prevent rotation of the collet and maintain axial alignment. Motor position sensors or encoders may be included for monitoring open and closed positions of the collet.

The system may further include a controller configured to record user access data, timestamps, and instrument status into a tamper-resistant data log, such as a secure digital ledger or blockchain-based architecture for ensuring data integrity. In some embodiments, an artificial intelligence (AI) module analyzes recorded data to identify usage patterns, predict maintenance or replacement needs, and generate alerts for overuse, missing instruments, or irregular activity.

In other embodiments, a method corresponding to operation of the system is provided, including providing at least one rotary instrument and at least one rotary instrument stored therein. The method includes authenticating a user, verifying authorization, controlling the collet to release or secure an instrument, and recording transaction data. The method may further include steps of analyzing usage information, generating maintenance predictions, and providing visual or electronic alerts in response to system or user events.

Through the combination of secure mechanical retention, intelligent digital control, and automated data analysis, the invention offers a comprehensive solution for instrument management, reduced tool loss, improved workflow efficiency, and increased user accountability across dental, surgical, and/or educational applications.

These and other features of the present subject matter will become readily apparent upon further review of the following specification.

BRIEF DESCRIPTION OF DRAWINGS

FIG. 3 is a block diagram illustrating an example electronic architecture of the rotary instrument storage, monitoring, and access control system.

Similar reference characters denote corresponding features consistently throughout the attached drawings.

DETAILED DESCRIPTION

Figures 1A, 1B, 1C, 1D:
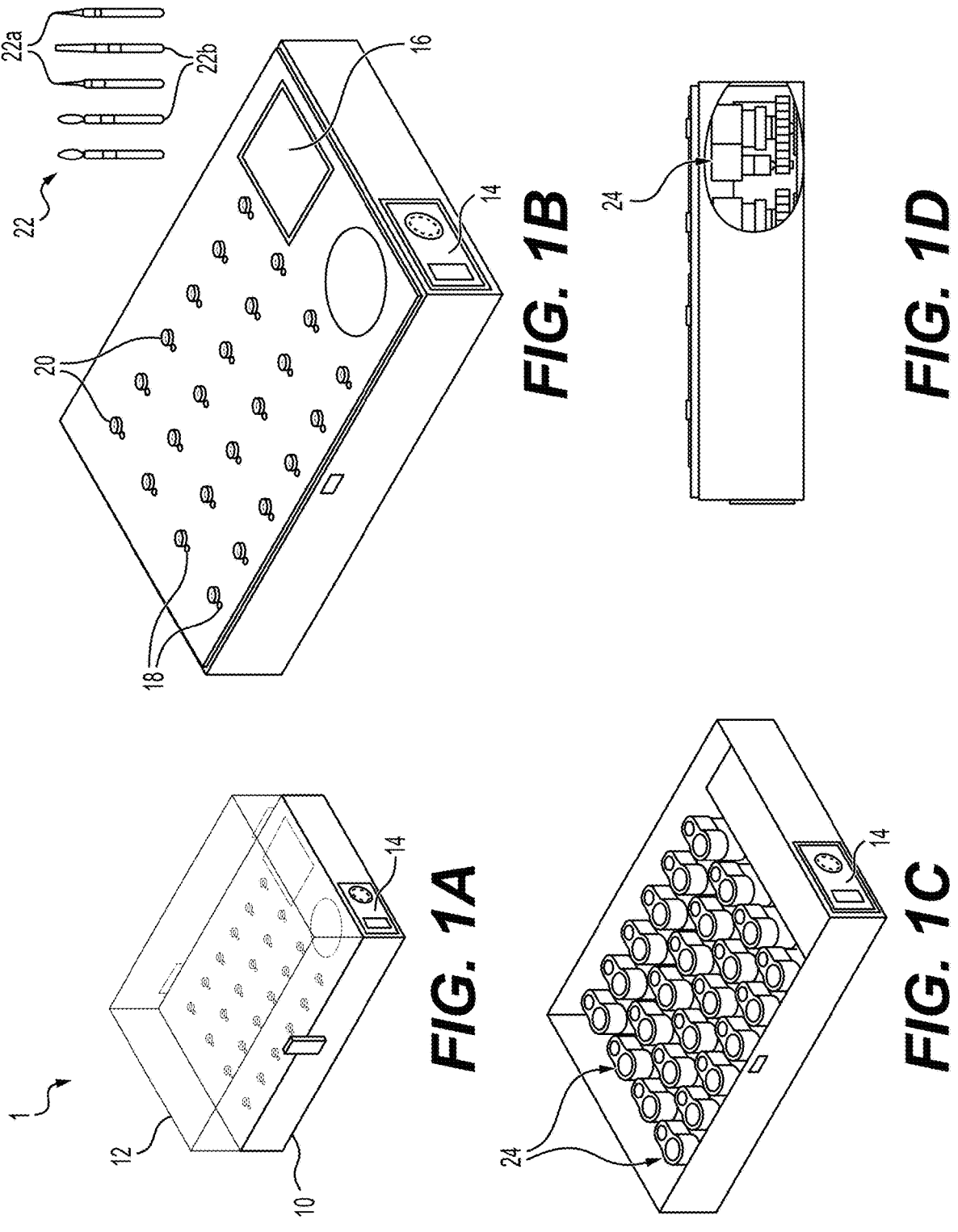
FIG. 1A is a perspective view of a rotary instrument storage, monitoring, and access control system.
FIG. 1B is a perspective view of a base of the system of FIG. 1A, as well as non-limiting exemplary rotary instruments stored by the system.
FIG. 1C is a perspective cutaway view of multiple collet assemblies arranged in the base of FIG. 1A and FIG. 1B.
FIG. 1D is a side view with cutout showing the internal positioning of a collet assembly in the system of FIGS. 1A-C.

Referring now to FIGS. 1A-1D, there is illustrated an exemplary embodiment of a system 1 for storage, monitoring, and access control of rotary instruments. The system 1 includes a base 10 configured to house a plurality of collet assemblies 24 that are each adapted to receive and secure a rotary instrument 22, such as a dental bur, drill bit, or similar precision tool. The base 10 may be enclosed by a transparent cover 12 that allows for visual inspection of the instruments while preventing unauthorized or accidental access when closed. The cover 12 may be pivotally or removably attached and include one or more sensors configured to detect whether it is in an open or closed state, thereby enabling or disabling release operations accordingly. In a particular embodiment, collet assemblies 24 automatically clamp onto rotary instruments 22 when cover 12 is in a closed state, thereby preventing falling of the rotary instruments 22 during transport of the system 1.

As shown in FIGS. 1A and 1B, the base 10 supports an array of slots 20, each of which corresponds to a collet assembly 24 that secures a holding end 22b of a respective rotary instrument 22, leaving a working end 22a exposed for identification. Each slot 20 may be associated with a visual indicator 18, such as a multicolor LED, that communicates the status of the corresponding instrument or collet assembly. Non-limiting examples of the status of the corresponding instrument or collet assembly include available, in use, missing, error, or maintenance-required. A display 16 mounted on or integrated with the base 10 may provide visual output of system information, including user identification, authentication prompts, and instrument inventory data.

An authorization system 14 is operatively connected with a controller and the collet assemblies 24 and configured to verify a user's identity and access level prior to instrument release. The authorization system 14 may include one or more authentication mechanisms, non-limiting examples of which include a fingerprint scanner, RFID reader, facial recognition sensor, passcode input, or combinations thereof. Upon successful user verification, the controller communicates with the appropriate collet assembly 24 to release a single authorized instrument 22. In some embodiments, the controller may restrict subsequent releases until a previously removed instrument is returned to its assigned collet, thereby ensuring accountability and accurate tracking of tool usage.

FIG. 1C shows an example configuration with multiple collet assemblies 24 arranged in a matrix or grid pattern within the base 10, each assembly 24 individually and electronically controllable. As is well known, internal wiring or printed circuit routing (not shown) beneath the collet assemblies may be included to interconnect the actuators, sensors, and LED indicators 18 with the controller and power source of the system. Each collet assembly 24 is configured, as described in greater detail in FIGS. 2A-E, to clamp or release the rotary instrument 22 through a motor-driven cam and collet mechanism.

FIG. 1D provides a side view of the system 1 showing the relative positioning of the collet assemblies 24 within the base 10. The modular design of the collet assemblies facilitates maintenance, cleaning, and replacement while preserving precise alignment and secure mechanical engagement.

Figure 2B:
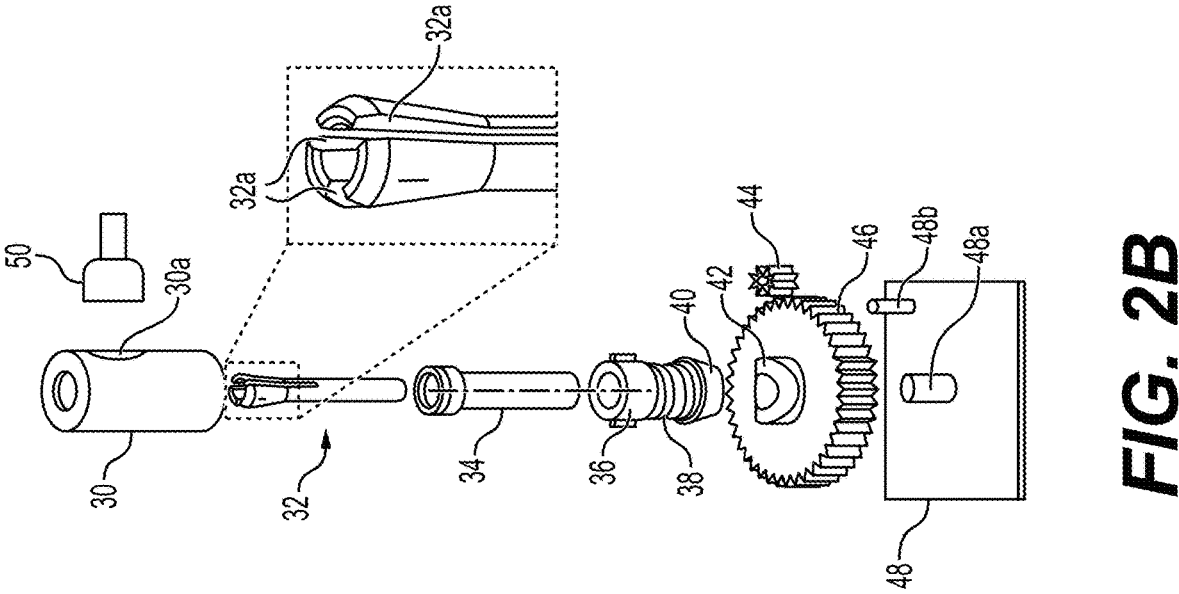
FIG. 2B is an exploded perspective view showing select components of a collet assembly.
Figure 2A:
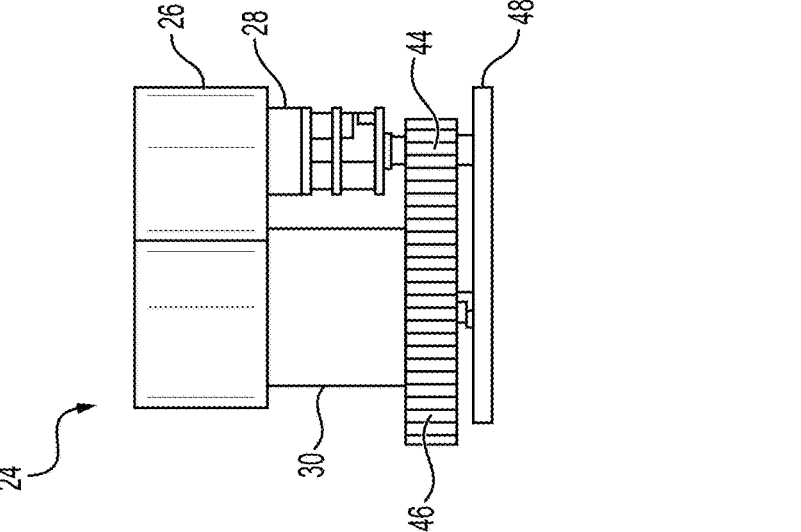
FIG. 2A is a side view of a collet assembly.

Referring now to FIGS. 2A-2E, further details of an example collet assembly 24 are provided. As shown in FIG. 2A, the collet assembly 24 includes an uppermost sleeve 26 enclosing a drive motor or servo 28, collet sleeve 30, and sensor 50 positioned over a collet 32. The collet 32 is formed with multiple longitudinal slots 32a that permit radial expansion and contraction, thereby allowing it to grip or release the holding end 22b (see FIG. 1B) of a rotary instrument under controlled actuation.

In FIG. 2B, an exploded view of the collet assembly 24 is shown. The collet 32 is supported within a collet holder 34 and guided by an anti-rotational guide 36 that ensures linear, non-rotational movement. Anti-rotational guide 36 is provide with, for example, male protrusions as shown which fit into corresponding slots (not shown) within collet sleeve 30. A spring 38 biases the collet 32 toward an open position, facilitating automatic release when no clamping force is applied. A cam follower 40 interfaces with a cam 42 to convert rotary motion into linear displacement. The cam 42 is mounted to spur gear 46 and driven by pinion gear 44 through motor 28. Spur gear 46 and pinion gear 44 are mounted to base plate 48 via respective vertical shafts 48a, 48b. The gearing arrangement provides mechanical advantage and precise motion control for advancing or retracting collet holder 34 and thereby opening and closing collet 32.

Figures 2C, 2D, 2E:
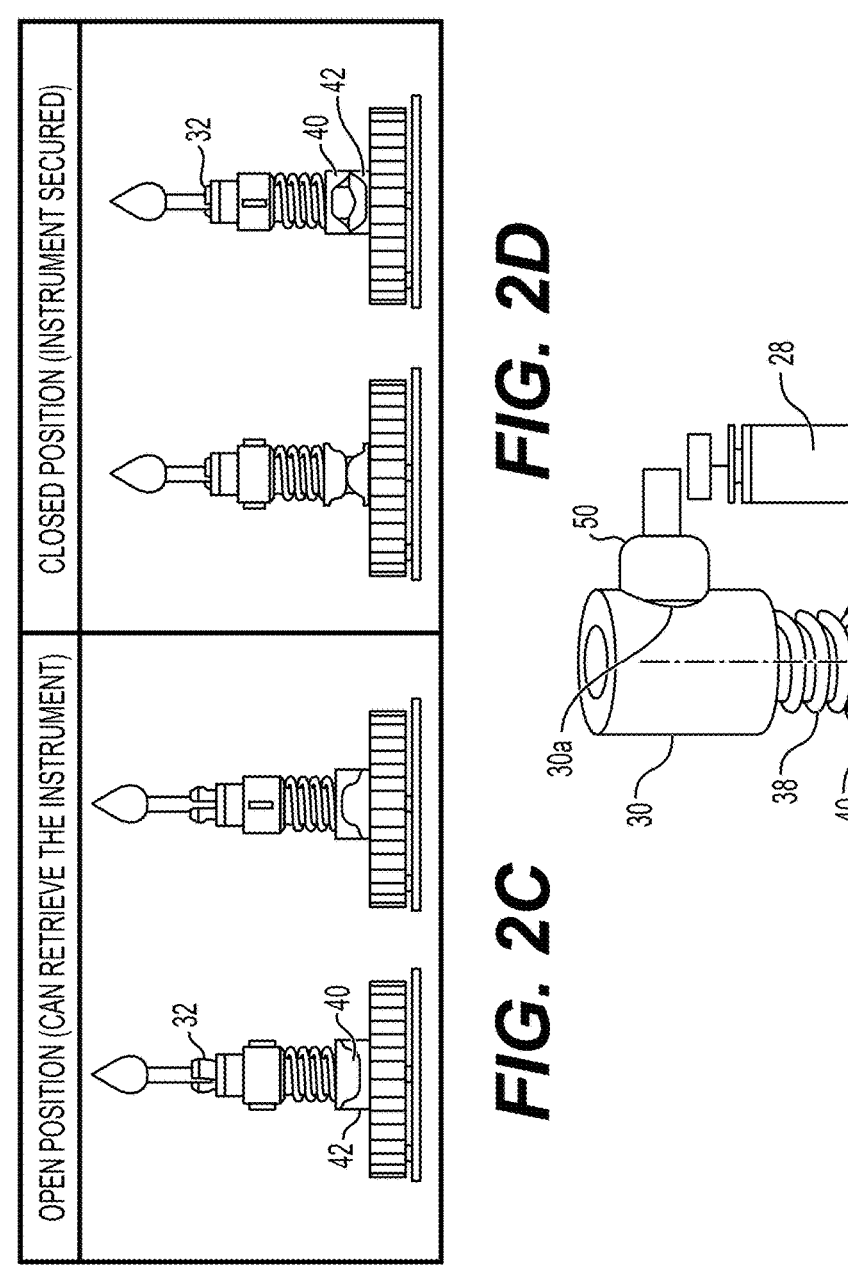
FIG. 2C is a schematic view of a collet assembly in an open position in which a cam follower is lowered.
FIG. 2D is a schematic view of a collet assembly in a closed position in which a cam follower is raised.
FIG. 2E is a perspective view of an assembled collet mechanism with upper sleeve removed showing motor and sensor placement of the assembly.

To provide positional feedback and error detection, the collet assembly 24 further includes sensor 50, as depicted in FIGS. 2B and 2E. The sensor 50 is configured to detect the operational state of the collet, such as open, closed, or error, and to transmit corresponding signals to the controller. In various non-limiting embodiments, the sensor 50 may comprise an infrared IR beam sensor, a Hall-effect sensor paired with a magnet, or another non-contact position sensor. The sensor 50 enables the system to confirm successful instrument engagement or release, detect jams or misalignments, and log collet state data for diagnostic or maintenance purposes.

FIGS. 2C and 2D illustrate the two principal operating positions of the collet assembly 24. In FIG. 2C, the cam follower 40 is in its lowered position, mated with the cam 42 such that the collet 32 is open, allowing the rotary instrument to be retrieved or inserted. In FIG. 2D, the cam follower 40 is raised, compressing the collet 32 to grip the rotary instrument securely in the closed position. As the drive motor 28 rotates, the pinion gear 44 turns the spur gear 46, causing the cam 42 to raise or lower the cam follower 40. Downward movement of the cam follower allows the collet 32 to expand to an open position, while upward movement compresses the slotted structure of the collet 32 to securely clamp the rotary instrument 22 in a closed position.

Finally, FIG. 2E provides a perspective view of the assembled collet mechanism, showing the integrated arrangement of the drive motor 28, gears 44, 46, cam 42, cam follower 40, spring 38, and collet sleeve 30, along with the position sensor 50 disposed adjacent the motor or mechanical interface to detect the current state of the collet through a window 30a formed in collet sleeve 30.

Referring now to FIG. 3, there is illustrated a block diagram of the electronic control architecture used by the system 1. The electronic components are centered around a controller 100 that coordinates the various subsystems, including authentication, sensing, actuation, display, and power management functions. The controller 100 may comprise a microcontroller, microprocessor, or embedded computing module programmed to execute logic for user access control, motor actuation, and data management. The controller 100 manages signals from peripheral components, drives the collet actuators, and controls LED color states via, for example, pulse-width modulation PWM or other techniques. In certain embodiments, the controller performs artificial intelligence AI-based analysis of instrument usage data to predict maintenance needs or detect anomalies, and may log operational data using a secure, blockchain-inspired hash-chain protocol to ensure data integrity and traceability.

User authentication system 102 communicates with controller 100 to verify user identity prior to enabling access to a rotary instrument. user authentication system 102 may include multiple verification modules such as an RFID reader 102*a* for card or tag-based access, a fingerprint scanner 102*b* for biometric identification, and a passcode entry module 102*c* for manual code input. These subsystems 102*a-c* may operate independently or in combination, providing tiered security levels or multi-factor authentication.

One or more sensor subsystems 104 are included in connection with controller 100 for monitoring physical and environmental conditions. The sensor subsystems 104 may include a bur presence sensor 104*a*, which may be an infrared IR or Hall-effect sensor as previously discussed; a motor encoder sensor 104*b* for confirming rotational position and operational status of the motor; a cover position sensor 104*c* for determining whether the transparent protective cover 12 is open or closed; and a real-time clock RTC 104*d* for timestamping user interactions and system events.

A power management system 106 provides power distribution and backup functionality for the device. It may include a USB or adapter-based power input and a rechargeable battery backup, allowing uninterrupted operation and data preservation in the event of external power loss.

An LED indicator system 108 is coupled to the controller 100 to provide visual feedback to the user. As mentioned previously, each instrument slot may include a dedicated RGB LED capable of displaying different colors corresponding to operational states. For example, green to indicate availability, orange to indicate in use, yellow for worn or maintenance-required instruments, red for unauthorized access, and flashing red for system errors. These non-limiting example LED indicators are provided in Table 1 below

TABLE 1

| LED Color | Meaning |
| --- | --- |
| Green | Instrument present and available |
| Orange | Instrument currently checked out |
| Yellow | Worn—inspection or replacement recommended |
| Red | Unauthorized user or restricted access |
| Flashing Red | Error or sensor malfunction |
| Blue | Slot highlighted for user guidance |
| Off | Idle or cover closed |

The system further includes a display and communication interface 110 providing an interactive user interface and data communication. The interface 10 may include an LCD or touch display for presenting status information, authentication prompts, and maintenance alerts. A USB-C or wireless communication link may be included for data export, external diagnostics, or network integration with institutional inventory systems.

Each access event of a rotary instrument may be recorded by the system as a digital [0041] record containing, for example, user ID, instrument ID, timestamps, sensor confirmations, and a hash of the previous record. This creates a chained data structure such that modification of any prior entry invalidates subsequent hashes, ensuring tamper-evident storage. The chain may be stored locally in memory or exported for audit verification.

Collectively, the elements illustrated in FIG. 3 provide an intelligent electronic framework for secure control and monitoring of the system 1. Through integration of user authentication, sensor feedback, and AI-driven data analysis, the controller 100 enables precise management of the rotary instruments, enforces access rules, records authenticated transactions, and ensures reliable operation.

Figure 4:
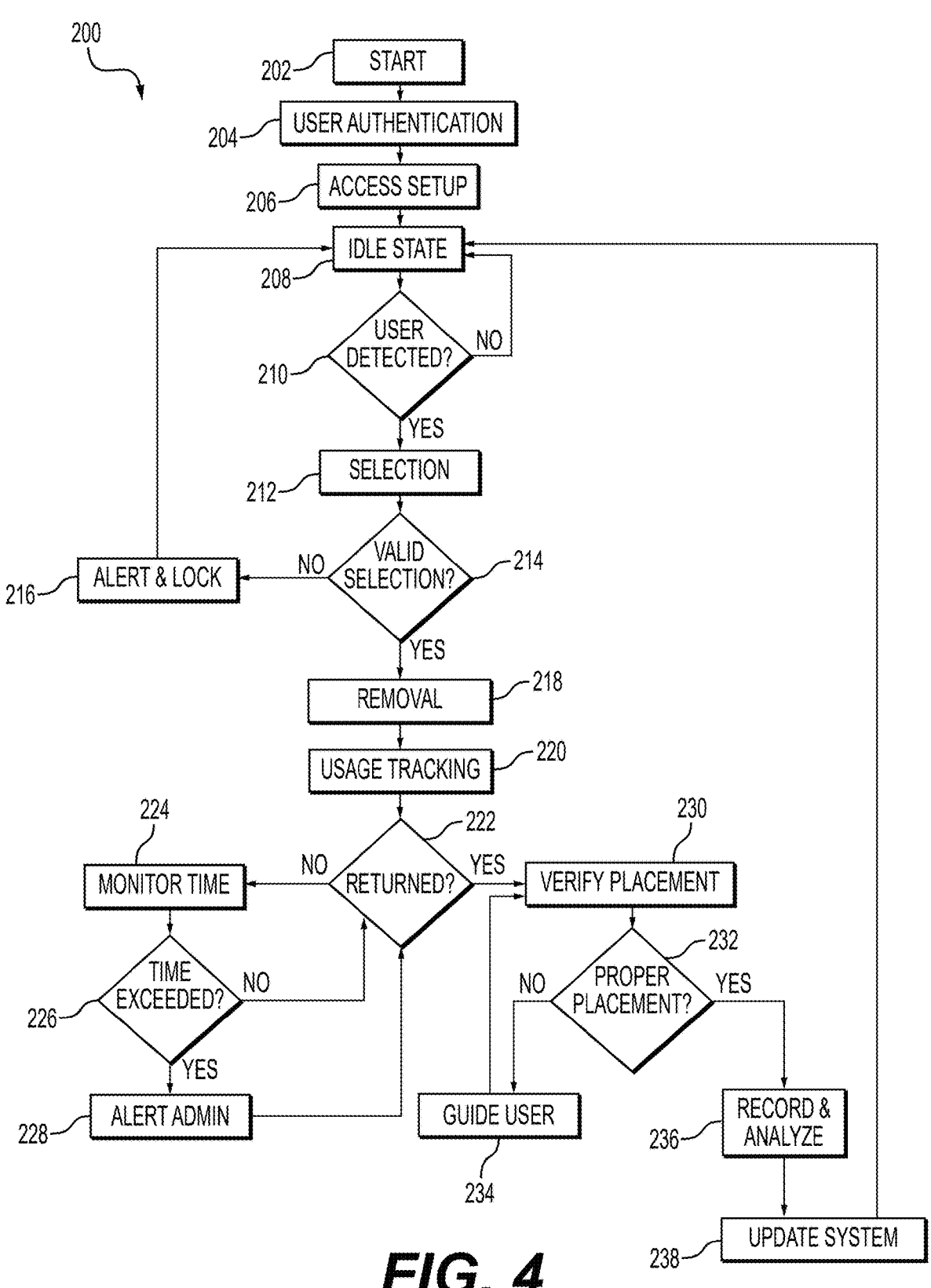
FIG. 4 is a flowchart illustrating an example operational process of the rotary instrument storage, monitoring, and access control system.

Referring now to FIG. 4, there is shown a system operation flowchart 200 depicting an exemplary sequence of operations for the rotary instrument storage, monitoring, and access control system 1. The flowchart illustrates how the system integrates user authentication, access control, sensor feedback, and data processing to manage the retrieval, usage, and return of rotary instruments in a controlled and traceable manner.

The operation begins at step 202—Start, followed by step 204—User Authentication, in which the system verifies a user's identity through the authentication subsystem 102, as previously described. Authentication may be achieved via RFID scanning, fingerprint recognition, passcode entry, or a combination thereof. Upon successful authentication, the system proceeds to step 206—Access Setup, during which the controller 100 configures appropriate access permissions and activates a relevant collet assembly corresponding to the authorized user's access level or pre-assigned instrument.

After setup, the system enters an idle state 208, awaiting user interaction or sensor input. When a user's hand or presence is detected near the instrument area, as determined by proximity or infrared sensors, the system advances to step 210—User Detection. If no user is detected, the system remains in the idle state to conserve power and maintain security. In various embodiments, user detection may be achieved through one or more proximity-sensing techniques. For example, an infrared proximity sensor or time-of-flight distance sensor positioned near the instrument area may detect motion or the approach of a user's hand within a predetermined range. Alternatively, a capacitive touch or field-effect sensor embedded around the housing surface may sense changes in capacitance caused by a user's hand. An ultrasonic range sensor may also be used and/or a camera or optical sensor capable of identifying user motion or hand position.

Once a user is detected, the process continues to step 212—Selection, where the user selects a rotary instrument for removal. The system verifies whether the selection corresponds to an authorized or valid instrument in decision step 214 (Valid Selection?). If the selection is invalid or unauthorized, the system triggers step 216—Alert and Lock, which may include visual or audible alerts and a temporary lockout of further access. If the selection is valid, the controller signals the corresponding collet assembly to release the chosen instrument at step 218—Removal.

Upon removal, the system initiates step 220 (Usage Tracking), wherein data such as user identity, time of removal, and collet status are recorded. The controller (100), in conjunction with the AI module, may monitor instrument usage duration and detect operational irregularities for maintenance prediction.

The next stage involves determining whether the instrument has been returned at decision step 222 (Returned?). If the instrument has not been returned, the system enters step 224—Monitor Time, tracking elapsed duration since removal. If the time exceeds a predefined threshold as determined in step 226 (Time Exceeded?), the system executes step 228—Alert Admin, to notify administrators of a missing or overdue instrument via system log, LED indication, or network alert.

If the instrument is detected as returned, the process proceeds to step 230—Verify Placement, where sensors such as the presence detector and position sensor confirm proper reinsertion. A subsequent check at step 232 (Proper Placement?) determines whether the instrument is correctly seated and secured. If misalignment or incorrect placement is detected, the system activates step 234—Guide User, providing visual or textual prompts via the display interface to assist the user in proper reinsertion.

Once correct placement is verified, the process advances to step 236 (Record and Analyze), where all event data are stored in a secure digital ledger. The AI module may further analyze usage data to identify trends in wear, maintenance frequency, or user behavior. Finally, at step 238 (Update System), the AI and data systems are updated or retrained using the newly logged data, ensuring improved predictive accuracy, performance optimization, and auditability across subsequent operations.

The AI analysis module may execute rule-based or statistical algorithms comparing recorded parameters such as total checkout count, cumulative usage duration, number of distinct users, and time-based patterns. Thresholds may trigger maintenance alerts: for example, when checkout count exceeds fifty uses or cumulative time exceeds forty hours, the system may display a yellow or orange LED and notify an administrator. Data analytics may also identify anomalies such as unusually long checkouts or rapid repeated access, prompting administrative review.

The AI system may further perform anomaly detection and user-behavior analysis. Anomalies may include excessive checkout durations, repeated failed authentications, or inconsistent sensor readings (e.g., instrument missing while lock closed). The AI compares real-time data against learned user patterns to flag deviations and automatically notify administrators. In educational environments, user behavior analysis may track student proficiency and adherence to prescribed procedural sequences.

In alternative embodiments, the system may communicate wirelessly with external laboratory management platforms for centralized reporting. Additional modules such as accelerometers, vibration sensors, or temperature probes integrated with the handpiece could enable real-time detection of active cutting versus idle time, further enhancing predictive maintenance accuracy.

Collectively, the operational flow of FIG. 4 demonstrates how the system (1) employs real-time sensing, authentication control, and AI-driven analytics to automate the secure distribution, monitoring, and lifecycle management of rotary instruments. This closed-loop process enhances user accountability, minimizes instrument loss, and supports predictive maintenance through continuous learning and adaptive data analysis.

While specific embodiments of the invention have been described and illustrated, it will be appreciated that s modifications, variations, and alternative configurations may be devised without departing from the scope of the invention. Features described in connection with one embodiment may be combined with those of other embodiments where technically feasible. The inventive concepts disclosed herein are intended to encompass not only the particular structures and methods described, but also equivalents thereof, as well as future implementations that employ substantially the same underlying principles for secure, intelligent management of precision rotary instruments.

It is to be understood that the rotary instrument storage, monitoring, and access control system is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A system for storage of a rotary instrument comprising:
   at least one rotary instrument, the at least one rotary instrument having a working end and a holding end;
   a base comprising at least one collet, the at least one collet configured to secure or release the holding end of the at least one rotary instrument;
   a user authenticator configured to verify a user authorization; and
   a controller configured to signal the at least one collet to secure or release the at least one rotary instrument upon receiving verification from the user authenticator if a user is authorized for removal of the at least one rotary instrument.

2. The system of claim 1, wherein the user authenticator is selected from the group consisting of: a fingerprint reader, a radio-frequency identification (RFID) reader, a facial recognition sensor, a passcode entry device, and combinations thereof.

3. The system of claim 1, wherein the at least one rotary instrument comprises two or more rotary instruments, and the base comprises at least two respective collets for the two or more rotary instruments, and wherein the controller is configured to permit a user to remove only one rotary instrument at a time until a previously removed rotary instrument is returned to its respective collet.

4. The system of claim 1, further comprising at least one sensor configured to detect a presence or absence of the at least one rotary instrument within a corresponding collet.

5. The system of claim 4, wherein the controller is further configured to generate an alert if the at least one rotary instrument is absent or incorrectly inserted into the corresponding collet.

6. The system of claim 1, further comprising a visual indicator associated with the at least one collet, the visual indicator comprising a light-emitting diode (LED) that changes color to indicate one or more conditions of the at least one collet selected from the group consisting of: available, in use, worn, unauthorized, an error condition, and combinations thereof.

7. The system of claim 1, further comprising a transparent protective cover configured to restrict access to the at least one rotary instrument when the transparent protective cover is closed, and a sensor configured to detect whether the transparent protective cover is open or closed.

8. The system of claim 1, wherein the controller is configured to record user identification data and rotary instrument access events in a data log stored on a secure digital ledger.

9. The system of claim 1, further comprising an artificial-intelligence (AI) module configured to analyze rotary instrument usage patterns and predict maintenance or replacement needs.

10. The system of claim 1, wherein the at least one collet is actuated between a secure position and a release position by a cam-driven mechanism.

11. The system of claim 10, wherein the cam-driven mechanism comprises a spur gear having a cam profile on an upper surface, the cam profile configured to lift or lower a collet holder to respectively release or secure the at least one rotary instrument.

12. The system of claim 11, wherein the spur gear is driven by an electric motor.

13. The system of claim 10, wherein the collet comprises a slotted structure that radially compresses around the holding end of the at least one rotary instrument when driven axially into a collet holder.

14. The system of claim 13, wherein the collet is biased toward an open position by a spring and transitions to a closed position when the collet holder is linearly advanced by the cam-driven mechanism.

15. The system of claim 10, further comprising an anti-rotational guide configured to prevent rotation of a collet holder while permitting vertical translation.

16. A method for secure storage and controlled access of a rotary instrument, the method comprising:

providing a system for storing at least one rotary instrument and at least one rotary instrument stored therein;

receiving, by a user authenticator, an authentication request from a user;

verifying, by the user authenticator, a user authorization;

transmitting, by the user authenticator, a verification signal to a controller; and upon determining that the user is authorized, signaling, by the controller, at least one collet to release a holding end of the at least one rotary instrument.

17. The method of claim 16, further comprising recording user identification data, time of access, and rotary instrument status in a data log stored on a tamper-resistant ledger or blockchain database.

18. The method of claim 16, further comprising detecting presence or absence of a rotary instrument using at least one sensor associated with the at least one collet.

19. The method of claim 16, further comprising analyzing recorded usage data with an artificial-intelligence module to predict rotary instrument wear or maintenance requirements.

20. The method of claim 16, further comprising illuminating an LED indicator associated with the at least one collet to indicate rotary instrument status during retrieval or return, and restricting access such that only one rotary instrument is released at a time until a previously released rotary instrument is returned.

* * * * *